(12) United States Patent
Wang et al.

(10) Patent No.: US 11,957,404 B2
(45) Date of Patent: Apr. 16, 2024

(54) TWO-STAGE ELECTROSURGICAL DEVICE FOR VESSEL SEALING

(71) Applicant: GYRUS ACMI, INC., Westborough, MA (US)

(72) Inventors: Huisun Wang, Maple Grove, MN (US); Kester Julian Batchelor, Mound, MN (US); William Butler, Minneapolis, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

(21) Appl. No.: 17/929,430

(22) Filed: Sep. 2, 2022

(65) Prior Publication Data

US 2023/0044200 A1    Feb. 9, 2023

Related U.S. Application Data

(63) Continuation of application No. 15/602,607, filed on May 23, 2017, now Pat. No. 11,464,561.
(Continued)

(51) Int. Cl.
*A61B 18/14* (2006.01)
*A61B 17/285* (2006.01)
(Continued)

(52) U.S. Cl.
CPC ........ *A61B 18/1445* (2013.01); *A61B 17/285* (2013.01); *A61B 17/29* (2013.01);
(Continued)

(58) Field of Classification Search
CPC ........ A61B 18/1445; A61B 2017/2825; A61B 2018/00589; A61B 2018/00595;
(Continued)

(56) References Cited

U.S. PATENT DOCUMENTS

| 763,226 A | 6/1904 | Walden |
| 2,092,905 A | 9/1937 | Brumbelow |

(Continued)

FOREIGN PATENT DOCUMENTS

| EP | 2092905 A1 | 8/2009 |
| EP | 2353535 A1 | 8/2011 |

(Continued)

OTHER PUBLICATIONS

"U.S. Appl. No. 15/602,607, Advisory Action dated Aug. 6, 2020", 5 pgs.

(Continued)

*Primary Examiner* — Sean W Collins
(74) *Attorney, Agent, or Firm* — Schwegman Lundberg & Woessner, P.A.

(57) ABSTRACT

An end effector assembly of a forceps includes a first jaw with a tissue sealing surface and an electrode on the sealing surface, and a second jaw with a tissue sealing surface and an electrode on the sealing surface. The first jaw and the second jaw move between an open position and a closed position. The sealing surface of at least one of the first jaw and the second jaw has a rigid medial section and flexible lateral sections.

20 Claims, 9 Drawing Sheets

Related U.S. Application Data (60) Provisional application No. 62/344,751, filed on Jun. 2, 2016.

(51) Int. Cl.
*A61B 17/29* (2006.01)
*A61B 17/295* (2006.01)
*A61B 17/28* (2006.01)
*A61B 18/00* (2006.01)
*A61B 90/00* (2016.01)

(52) U.S. Cl.
CPC .... *A61B 17/295* (2013.01); *A61B 2017/2825* (2013.01); *A61B 2017/2926* (2013.01); *A61B 2018/00184* (2013.01); *A61B 2018/00589* (2013.01); *A61B 2018/00601* (2013.01); *A61B 2018/0063* (2013.01); *A61B 2018/1455* (2013.01); *A61B 2018/1465* (2013.01); *A61B 2090/034* (2016.02)

(58) Field of Classification Search
CPC .......... A61B 2018/00601; A61B 2018/00607; A61B 2018/0063; A61B 2018/126; A61B 2018/1455
See application file for complete search history.

(56) References Cited

U.S. PATENT DOCUMENTS

| | | | |
|---|---|---|---|
| 3,503,396 A | 3/1970 | Pierie et al. | |
| 5,693,051 A * | 12/1997 | Schulze | A61B 18/1206 606/41 |
| 5,728,121 A | 3/1998 | Bimbo et al. | |
| 5,752,973 A | 5/1998 | Kieturakis | |
| 5,754,928 A | 5/1998 | Moe et al. | |
| 6,086,586 A | 7/2000 | Hooven | |
| 6,113,598 A * | 9/2000 | Baker | A61B 18/1445 606/51 |
| 6,123,701 A | 9/2000 | Nezhat | |
| 6,406,485 B1 | 6/2002 | Hossain et al. | |
| 6,926,716 B2 | 8/2005 | Baker et al. | |
| 6,942,676 B2 | 9/2005 | Buelna | |
| 7,041,102 B2 | 5/2006 | Truckai et al. | |
| 7,182,775 B2 | 2/2007 | De Guillebon et al. | |
| 7,276,068 B2 | 10/2007 | Johnson et al. | |
| 8,192,433 B2 | 6/2012 | Johnson et al. | |
| 8,262,655 B2 | 9/2012 | Ghabrial et al. | |
| 8,298,232 B2 | 10/2012 | Unger | |
| 8,317,787 B2 | 11/2012 | Hanna | |
| 8,382,754 B2 | 2/2013 | Odom et al. | |
| 8,556,929 B2 | 10/2013 | Harper et al. | |
| 8,597,297 B2 | 12/2013 | Couture et al. | |
| 8,647,343 B2 | 2/2014 | Chojin et al. | |
| 8,795,274 B2 | 8/2014 | Hanna | |
| 8,945,125 B2 | 2/2015 | Schechter et al. | |
| 8,968,308 B2 | 3/2015 | Horner et al. | |
| 11,464,561 B2 | 10/2022 | Wang et al. | |
| 2002/0188294 A1 | 12/2002 | Couture et al. | |
| 2003/0171748 A1 | 9/2003 | Truckai et al. | |
| 2004/0143263 A1 | 7/2004 | Schechter et al. | |
| 2005/0203507 A1 | 9/2005 | Truckai et al. | |
| 2006/0217709 A1* | 9/2006 | Couture | A61B 18/1442 606/51 |
| 2007/0255279 A1 | 11/2007 | Buysse et al. | |
| 2009/0054894 A1 | 2/2009 | Yachi | |
| 2009/0149853 A1 | 6/2009 | Shields et al. | |
| 2009/0182333 A1 | 7/2009 | Eder et al. | |
| 2009/0216229 A1 | 8/2009 | Chojin | |
| 2010/0057083 A1 | 3/2010 | Hanna | |
| 2010/0057084 A1 | 3/2010 | Hanna | |
| 2011/0118736 A1 | 5/2011 | Harper et al. | |
| 2011/0190765 A1 | 8/2011 | Chojin | |
| 2011/0319886 A1* | 12/2011 | Chojin | A61B 18/1445 606/37 |
| 2013/0014375 A1 | 1/2013 | Hempstead et al. | |
| 2014/0155893 A1 | 6/2014 | Chojin et al. | |
| 2014/0257277 A1 | 9/2014 | Woloszko et al. | |
| 2014/0276731 A1 | 9/2014 | Voegele et al. | |
| 2015/0305796 A1 | 10/2015 | Wang | |
| 2016/0066980 A1* | 3/2016 | Schall | A61B 18/1442 606/45 |
| 2016/0346035 A1 | 12/2016 | Takei et al. | |
| 2017/0348044 A1 | 12/2017 | Wang et al. | |

FOREIGN PATENT DOCUMENTS

| | | |
|---|---|---|
| EP | 2554135 A1 | 2/2013 |
| EP | 3251623 A1 | 12/2017 |
| EP | 3251623 B1 | 4/2021 |
| WO | WO-9940861 A1 | 8/1999 |
| WO | WO-2007103986 A2 | 9/2007 |
| WO | WO-2007103986 A3 | 4/2008 |

OTHER PUBLICATIONS

"U.S. Appl. No. 15/602,607, Advisory Action dated Aug. 31, 2021", 3 pgs.
"U.S. Appl. No. 15/602,607, Examiner Interview Summary dated Jun. 23, 2021", 2 pgs.
"U.S. Appl. No. 15/602,607, Final Office Action dated Mar. 4, 2020", 12 pgs.
"U.S. Appl. No. 15/602,607, Final Office Action dated Mar. 30, 2022", 7 pgs.
"U.S. Appl. No. 15/602,607, Final Office Action dated Jun. 21, 2021", 12 Pgs.
"U.S. Appl. No. 15/602,607, Non Final Office Action dated Nov. 15, 2021", 7 pgs.
"U.S. Appl. No. 15/602,607, Non Final Office Action dated Nov. 19, 2019", 12 pgs.
"U.S. Appl. No. 15/602,607, Non Final Office Action dated Dec. 23, 2020", 10 pgs.
"U.S. Appl. No. 15/602,607, Notice of Allowance dated Jun. 3, 2022", 7 pgs.
"U.S. Appl. No. 15/602,607, Response filed Feb. 11, 2020 to Non Final Office Action dated Nov. 19, 2019", 18 pgs.
"U.S. Appl. No. 15/602,607, Response filed Mar. 15, 2022 to Non Final Office Action dated Nov. 15, 2021", 9 pgs.
"U.S. Appl. No. 15/602,607, Response filed Mar. 23, 2021 to Non Final Office Action dated Dec. 23, 2020", 14 pgs.
"U.S. Appl. No. 15/602,607, Response filed May 18, 2022 to Final Office Action dated Mar. 30, 2022", 7 pgs.
"U.S. Appl. No. 15/602,607, Response filed Jul. 6, 2020 to Final Office Action dated Mar. 4, 2020", 13 pgs.
"U.S. Appl. No. 15/602,607, Response filed Aug. 23, 2021 to Final Office Action dated Jun. 21, 2021", 15 pgs.
"U.S. Appl. No. 15/602,607, Response filed Oct. 23, 2019 to Restriction Requirement dated Sep. 12, 2019", 9 pgs.
"U.S. Appl. No. 15/602,607, Restriction Requirement dated Sep. 12, 2019", 8 pgs.
"European Application Serial No. 17173962.6, Communication Pursuant to Article 94(3) EPC dated Oct. 25, 2018", 5 pgs.
"European Application Serial No. 17173962.6, Extended European Search Report dated Oct. 19, 2017", 11 pgs.
"European Application Serial No. 17173962.6, Response filed Feb. 11, 2019 to Communication Pursuant to Article 94(3) EPC dated Oct. 25, 2018", 2 pgs.
"European Application Serial No. 17173962.6, Response filed Jun. 5, 2018 to Extended European Search Report dated Oct. 19, 2017", 11 pgs.
"European Application Serial No. 17173962.6, Response filed Oct. 1, 2020 to Summons to Attend Oral Proceedings mailed Jun. 17, 2020", 50 pgs.
"European Application Serial No. 17173962.6, Summons to Attend Oral Proceedings mailed Jun. 17, 2020", 6 pgs.
"European Application Serial No. 21168117.6, Extended European Search Report dated Jul. 14, 2021", 11 pgs.

(56) References Cited

OTHER PUBLICATIONS

"European Application Serial No. 21168117.6, Response filed Mar. 8, 2022 to Extended European Search Report dated Jul. 14, 2021", 67 pgs.
Paul, Palinski J, et al., "CoPending PCT Pending Application PCT/US2016/012823 filed Jan. 11, 2016", 38 pgs.

* cited by examiner

TWO-STAGE ELECTROSURGICAL DEVICE FOR VESSEL SEALING

RELATED APPLICATION

This application claims the benefit of U.S. Provisional Patent Application No. 62/344,751, filed on Jun. 2, 2016.

The entire contents of the above application are incorporated herein by reference.

FIELD

The present disclosure relates to an electrosurgical device. More specifically, the present disclosure relates to an electrosurgical device for vessel sealing.

BACKGROUND

The statements in this section merely provide background information related to the present disclosure and may not constitute prior art.

Generally forceps may be utilized for laparoscopic surgery. The forceps may be employed to control delicate movements inside a patient and may include a gripping assembly or a cutting assembly. Further, the forceps may utilize electrical energy in the gripping assembly. Typically, the forceps have a pair of opposed resilient jaws that are closed against each other by pulling the jaws into a distal end of a shaft that captures a portion of the jaws that is wider than the distal end opening of the shaft so that the jaws are moved together. Similarly the shaft may be pushed over the jaws so that the jaws are moved together to create a gripping force. In both of these arrangements, the shaft captures the jaws and acts as a cam that forces the jaws together to create the gripping force.

Current bipolar electrosurgical sealing forceps employ a pair of jaws with RF energy to coagulate a vessel and further employ a moveable cutting blade to cut the sealed vessel after coagulation. Such devices, however, require a high jaw force to compress the vessel tissue for desired sealing results. The high jaw force can cause unwanted tissue damage, since, for example, the jaw force requirements for large vessels and small vessels are different.

Accordingly, there is a need in the art for electrosurgical forceps that can seal both large and small vessels.

SUMMARY

The present disclosure provides an end effector assembly with a two-stage configuration that optimally seals both small and large vessels.

Accordingly, pursuant to one aspect of the present invention, an end effector assembly of a forceps includes a first jaw with a tissue sealing surface and an electrode on the sealing surface, and a second jaw with a tissue sealing surface and an electrode on the sealing surface. The first jaw and the second jaw move between an open position and a closed position. The sealing surface of at least one of the first jaw and the second jaw has a rigid medial section and flexible lateral sections.

The foregoing aspect of the present invention can be further characterized by one or any combination of the features described herein, such as: the sealing surfaces of both the first jaw and the second jaw have a rigid medial section and flexible lateral sections; each lateral section has a cavity such that the lateral sections are cantilevered; the cavities are filled with a polymer; the medial section and the lateral sections are coplanar; each of the first jaw and the second jaw includes a jaw body and a sealing plate, the exterior surface of the sealing plate being the sealing surface of each of the first jaw and the second jaw; the jaw body of at least one of the first jaw and the second jaw includes a support member; a layer of pliable material is disposed between the support member and the sealing plate, the layer of pliable material being made of separate cells placed side by side with different stiffnesses, the center cells being more rigid than the lateral cells; the sealing plate of at least one of the first jaw and the second jaw has a central section connected to a central section of the respective jaw body, the lateral sections being cantilevered from the respective central section of the sealing plate; the lateral sections are chamfered and a wedge of compliant and electrically conductive material is disposed on the chamfer, the medial section and the lateral sections being coplanar; the medial section is a first plate and the lateral sections are a second plate that is coplanar with the first plate; non-conductive stops are disposed on the second plate that deflects the second plate prior to the first jaw and the second jaw closing; each of the first jaw and the second jaw has a first plate and a second plate; the non-conductive stops on one of the second plates deflects the second plates prior to the first jaw and the second jaw closing such that the medial plates contact each other; non-conductive stops are disposed on the first plate, the non-conductive stops of the second plate being longer than the non-conductive stops of the first plate such that the non-conductive stops of the second plate make contact before the non-conductive stops of the first plate make contact; the electrodes are connected to a source of electrosurgical energy, the source generating electrosurgical energy to coagulate tissue grasped between the first jaw and the second jaw; and at least one of the first jaw and the second jaw has a longitudinal slot and the end effector includes a blade that reciprocates within the slot.

Accordingly, pursuant to yet another aspect of the present invention, a method of using forceps includes one or more of the following steps: opening a first jaw and a second jaw of the forceps, the first jaw having a tissue sealing surface and an electrode on the sealing surface and the second jaw having a tissue sealing surface and an electrode on the sealing surface, the sealing surface of at least one of the first jaw and the second jaw has a rigid section and a flexible lateral; closing the first jaw and the second jaw to grasp tissue therebetween; applying electrosurgical energy to coagulate tissue grasped between the first jaw and the second jaw; and pressing the first jaw and the second jaw together to cut the tissue.

The method of using the forceps may be further characterized by one or any combination of the following features: the sealing surfaces of at least one of the first jaw and the second jaw has a rigid medial section and flexible lateral sections; the medial section is a first plate and the lateral sections are a second plate that is coplanar with the first plate; non-conductive stops are disposed on the second plate that deflects the second plate prior to the first jaw and the second jaw closing; each of the first jaw and the second jaw has a first plate and a second plate; the non-conductive stops on one of the second plates deflects the second plates prior to the first jaw and the second jaw closing such that the medial plates contact each other; non-conductive stops are disposed on the first plate, the non-conductive stops of the second plate being longer than the non-conductive stops of the first plate such that the non-conductive stops of the second plate make contact before the non-conductive stops of the first plate make contact; at least one of the first jaw and the second jaw has a longitudinal slot in which a blade reciprocates; and the method further includes applying electrosurgical energy to coagulate tissue grasped between the first jaw and the second jaw after closing the first jaw and the second jaw and before cutting the tissue.

Accordingly, pursuant to another aspect of the present invention, an end effector of a forceps includes a first jaw with a tissue sealing surface and an electrode on the sealing surface, a second jaw with a tissue sealing surface and an electrode on the sealing surface, and a blade that reciprocates within a longitudinal slot, the first jaw and the second jaw moving between an open position and a closed position. The sealing surfaces of at least one of the first jaw and the second jaw has a first section on a first side of the slot and a second section on a second side of the slot, the first section being a first plate and the second section being a second plate that is coplanar with the first plate, the first section being a rigid section and the second section being a flexible section.

The foregoing aspect of the present invention can be further characterized by one or any combination of the features described herein, such as: the sealing surfaces of both the first jaw and the second jaw have a rigid section on a first side of the slot and a flexible section on a second side of the slot; each of the first jaw and the second jaw includes a jaw body and a sealing plate, the exterior surface of the sealing plate being the sealing surface of each of the first jaw and the second jaw; and the jaw body of at least one of the first jaw and the second jaw includes a support member, a layer of pliable material being disposed between the support member and the sealing plate, the layer of pliable material being made of separate cells placed side by side with different stiffnesses, the center cells being more rigid than the lateral cells.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings.

DETAILED DESCRIPTION

The following description is merely exemplary in nature and is not intended to limit the present disclosure, application, or uses.

Referring now to the drawings, a forceps, such as, for example, a laparoscopic forceps, embodying the principles of the present invention is illustrated therein and designated at 2. The forceps 2 may function to grip an object. The forceps 2 may be used during surgery to grip a feature of interest including: a part of a body, an anatomical feature, tissue, veins, arteries, or a combination thereof. The forceps 2 may function to be used in surgery, for example, laparoscopic surgery. The forceps 2 may be used with or without power. Current may be passed through the forceps 2 so that the forceps are used for electrosurgery. For example, a therapy current may be passed from one jaw to a second jaw when tissue is located within the jaw and the therapy current may coagulate blood, cauterize, cut, or a combination thereof. The forceps 2 may generally include one or more working assemblies and sufficient controls to work the one or more assemblies. The forceps 2 may include parts employed to perform the recited functions and may include generally, a stylet (e.g., a tubular member, a hollow tube, or an assembly of tubes), a hand piece, one or more operable mechanisms used to actuate the stylet, or a combination thereof. The hand piece may be an assembly of parts or housing structures capable of forming a hand piece structure with a cavity. Note that the present invention is not limited to laparoscopic procedures. That is, the below described jaws can be employed with any type of medical device that clamps onto tissue.

Figure 1:
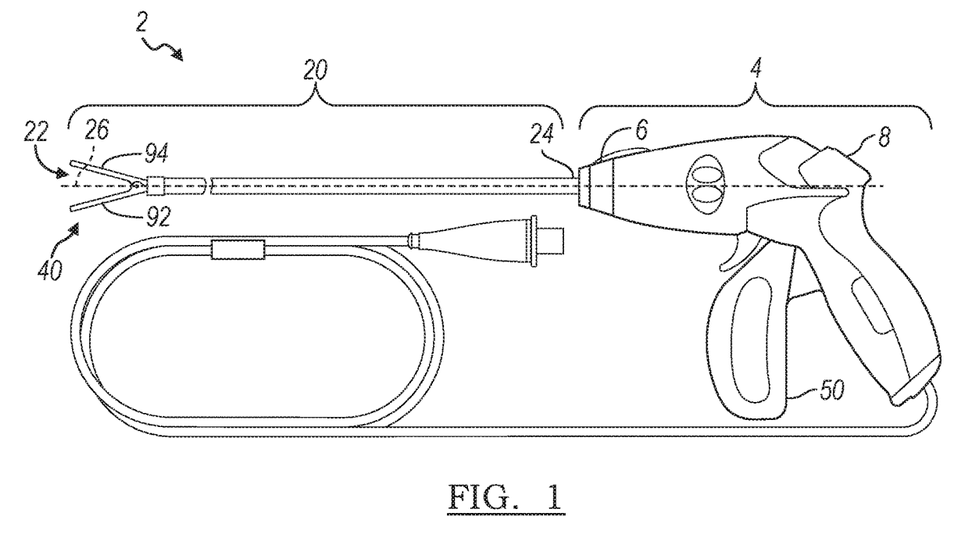
FIG. 1 illustrates an electrosurgical forceps in accordance with the principles of the present invention.

Turning now to FIG. 1, a side view of the forceps 2 is shown. The forceps 2 include a handpiece 4 having a distal end 6 and a proximal end 8. The handpiece 4 also includes at least one operable mechanism 50. A tubular member 20 has a proximal end 24 that is connected to the distal end 6 of the handpiece 4. The tubular member 20 includes a distal end 22 that includes jaws 40 extending therefrom. The jaws 40 have members 92 and 94 that open and close when the tubular member 20 is moved forward along the longitudinal axis 26 of the tubular member into contact with the members 92 and 94 or the jaws 40 are moved backwards along the longitudinal axis 26 into contact with the tubular member 20.

Figure 2:
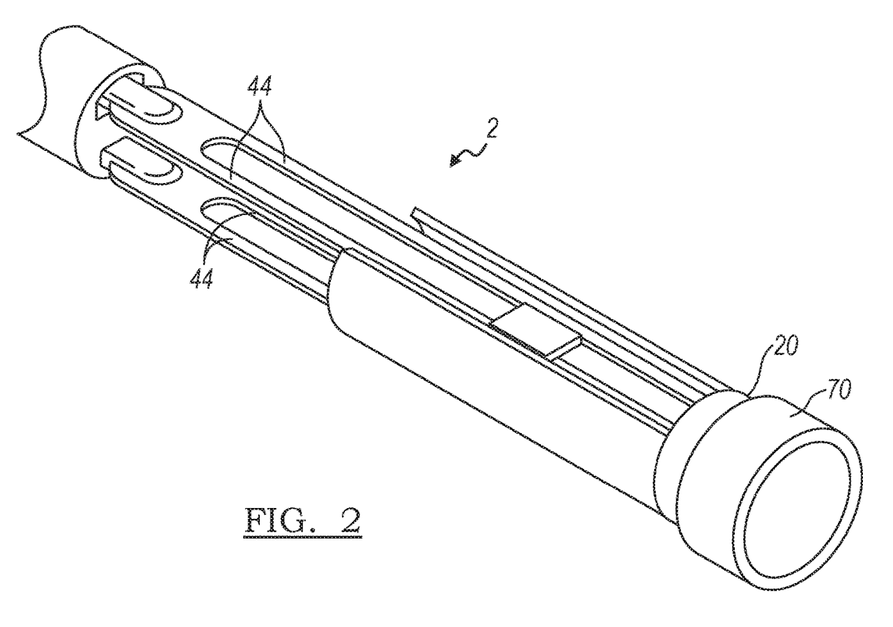
FIG. 2 an example of a set of jaws for the forceps shown in FIG. 1.
Figure 7:
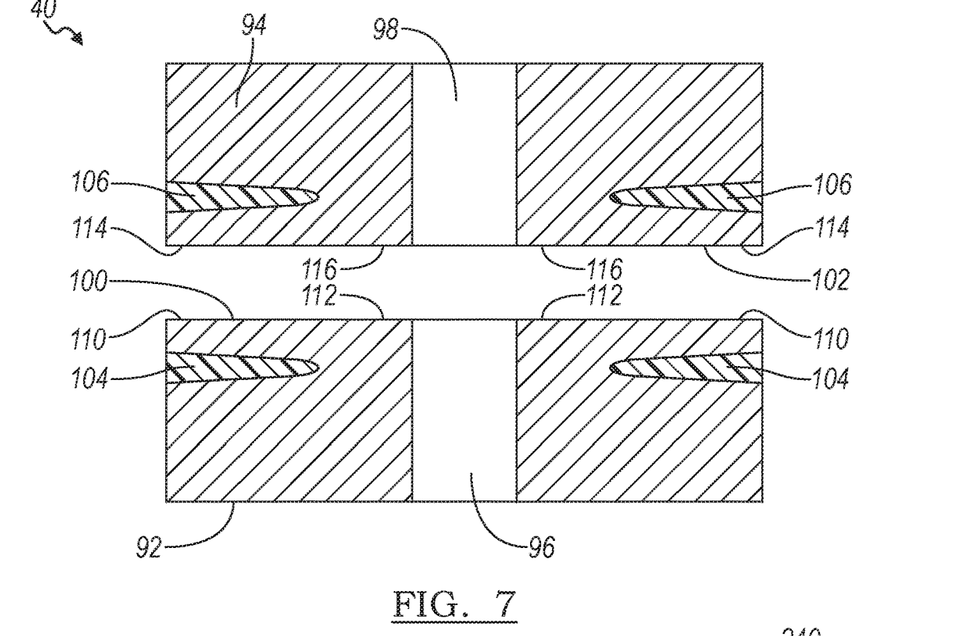
FIG. 7 illustrates a cross-sectional view of the jaws.

Referring further to FIGS. 2 and 7, a camming shaft 70 is located on the forceps 2 with the jaws 40 extending therefrom. The members 92 and 94 are biased by the camming shaft 70 so that the jaws 40 are opened and closed. The members 92 and 94 include inserts 104 and 106 and a pair of slots 96 and 98 that extend through the members 92 and 94, respectively. The inserts 104 and 106 are made of any suitable pliable material, such as, an elastic polymer. Accordingly, a sealing surface 100 of the member 92 includes a first sealing surface 110 on lateral cantilevered portions or sections of the member 92, that is, on both sides of the slot 96, and a second sealing surface 112 on medial portions or sections on both sides of the slot 96. The member 94 includes a first sealing surface 114 on lateral cantilevered portions or sections of the member 94, that is, on both sides of the slot 98, and a second sealing surface 116 on medial portions or sections on both sides of the slot 98. Note that the use of the inserts 104 and 106 is optional. Hence, without the use of the inserts 104 and 106, cavities would exist below the lateral cantilevered portions that define the first sealing surfaces 110 and 114. Also note that the inserts 104 and 106 and/or the cavities can extend along a portion of or all of the jaw members 92 and 94.

Figure 3:
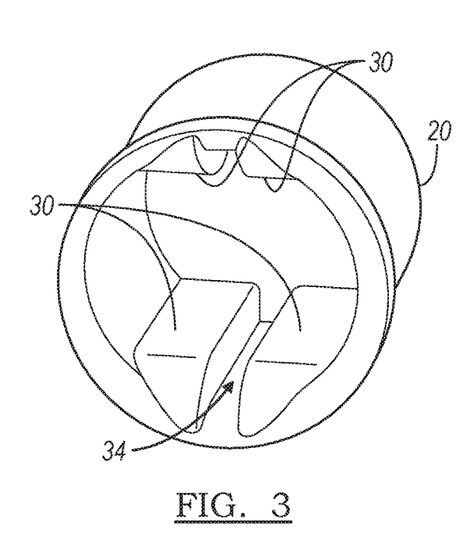
FIG. 3 illustrates an end of a tubular member and/or a camming shaft for the forceps.

FIG. 3 illustrates the end of the tubular member 20 or a camming shaft showing a pair of internal flat portions 30 along the top surfaces and the bottom surfaces. A blade recess 34 extends between the pair of internal flat portions 30 so that a blade 400 (FIGS. 11 and 12) extends out of the tubular member 20.

Figure 4:
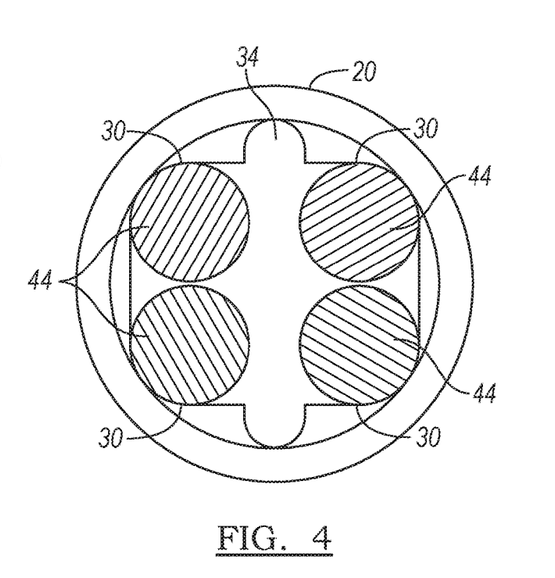
FIG. 4 illustrates an end view of a tubular member and/or a camming shaft.

FIG. 4 illustrates a cross-sectional view of a tubular member 20. The internal flat portions 30 include at least a portion that has a complementary shape to that of the legs of the jaws 44. Accordingly, as the tubular member 20 or the legs 44 axially move, the internal flat portions 30 control the orientation and movement of the jaws.

Figure 5:
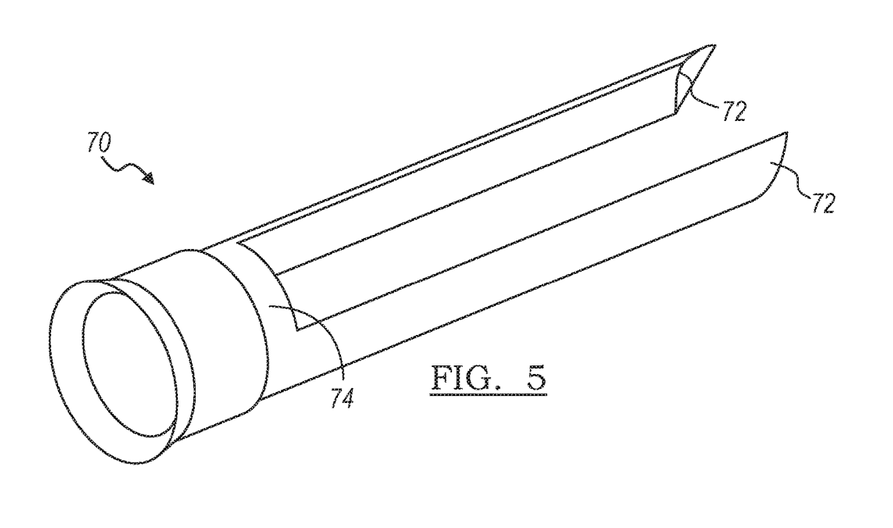
FIG. 5 illustrates a perspective view of a camming shaft.

FIG. 5 illustrates a perspective view of one example of a camming shaft 70 that is inserted into the tubular member 20. The camming shaft 70 includes a molded flare 74 with a pair of protrusions 72 extending therefrom.

Figure 6:
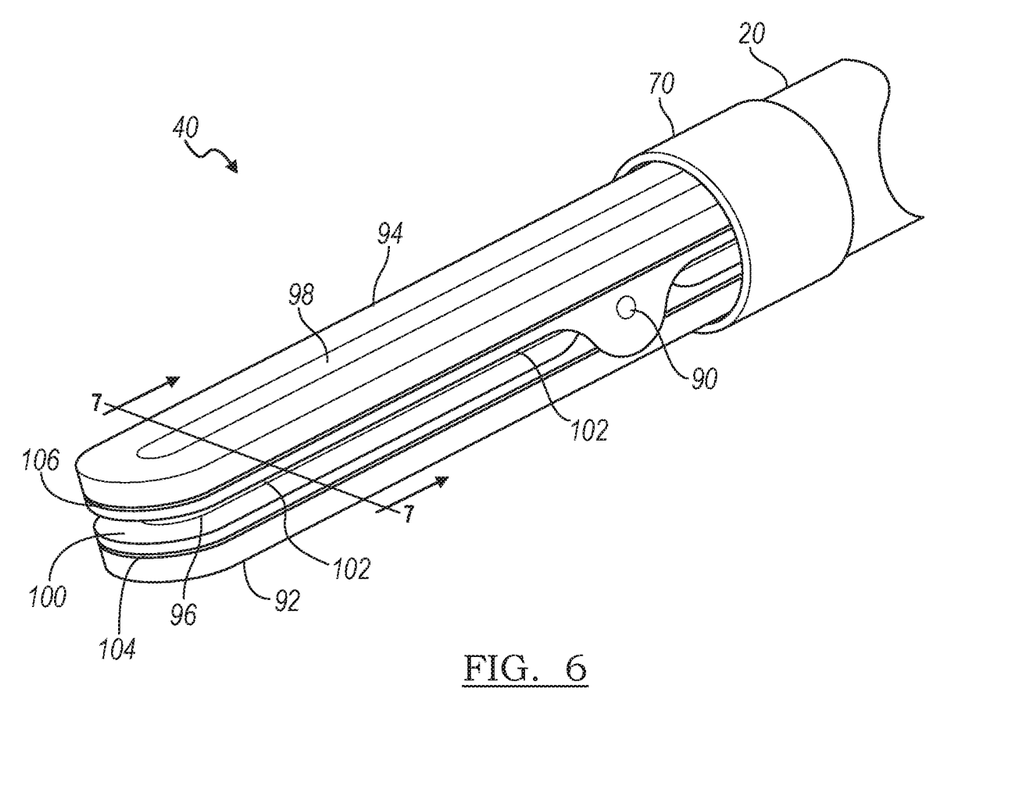
FIG. 6 illustrates a perspective view of the forceps shown in FIG. 1.

FIG. 6 illustrates the jaws 40 including a pin 90 located between the jaws. The pin 90 holds the jaw members 92 and 94 together and provide a pivot point for the jaw members 92 and 94 such that the members 92 and 94 close when the tubular member 20 is slid over the opposing members 92 and 94.

Turning back to FIG. 7, the first sealing surfaces 110 and 114 form a first compression zone above the inserts 104 and 106, and the second sealing surfaces 112 and 116 form a second compression zone when the jaw members 92 and 94 are clamped together on a vessel. As such, the jaws 40 is a two-stage end-effector with the first compression zones produced by the compression surfaces 110 and 114 being more flexible than the second compression zones produced by the compression surfaces 112 and 116.

In various arrangements, the jaw members 92 and 94 can be electrical connected to a generator that provides a source of electrosurgical energy so that a RF voltage with different potentials can be applied to the electrically connected sections of the jaw members 92 and 94. The RF voltage produces a current that passes from one jaw member to the other jaw member electrode through tissue, thereby heating the tissue to coagulate or cut the tissue.

Figure 8:
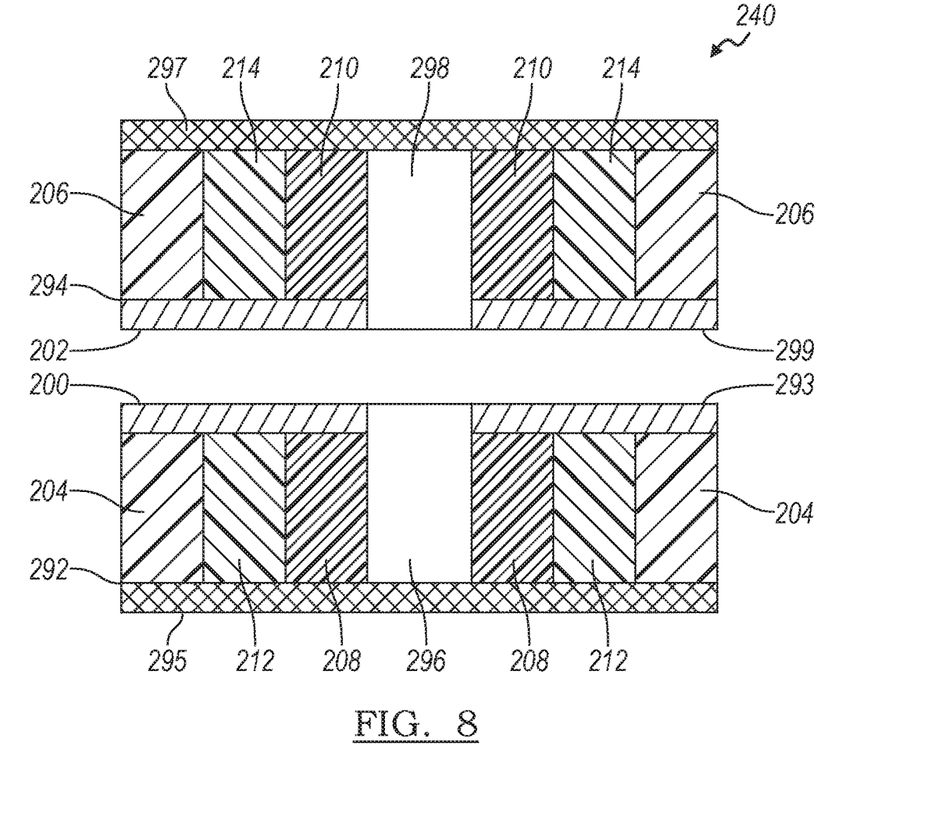
FIG. 8 illustrates a cross-sectional view of another set of jaws in accordance with the principles of the present invention.

Turning now to FIG. 8, there is shown another set of jaws 240 in accordance with the principles of the present invention. The jaws 240 include a first jaw member 292 and a second jaw member 294. The first jaw member 292 includes a jaw body or support member 295 and a sealing plate 293 disposed on both sides of a slot 296. The exterior surface of the sealing plate 293 defines a sealing surface 200. A layer of pliable material 204, 208 and 212 is disposed between the jaw body 295 and the sealing plate 293. The layer of pliable mater is made of separate cells placed side by side with different stiffnesses, the medial or center cells 208 being stiffer than the lateral cells 204. In certain arrangements, the layer of pliable material includes the medial cells 208 positioned adjacent to the lateral cells 204, while in other arrangements the intermediate cells 212 are positioned between the medial cells 208 and the lateral cells 204 to provide an additional transition from the stiffer medial cells 208 to the more flexible lateral cells 204.

The second jaw member 294 includes a jaw body 297 and a sealing plate 299 disposed on both sides of a slot 298. The exterior surface of the sealing plate 299 defines a sealing surface 202. A layer of pliable material 206, 210 and 214 is disposed between the jaw body 297 and the sealing plate 299. The layer of pliable mater is made of separate cells placed side by side with different stiffnesses, the medial or center cells 210 being stiffer than the lateral cells 204. In certain arrangements, the layer of pliable material includes the medial cells 210 positioned adjacent to the lateral cells 206, while in other arrangements the intermediate cells 214 are positioned between the medial cells 210 and the lateral cells 206 to provide an additional transition from the stiffer medial cells 210 to the more flexible lateral cells 206. The layers of pliable material 204, 208, 212 and 206, 210, 214 can extend along a portion of or all of the jaw members 292 and 294.

Accordingly, the sealing surfaces above the lateral cells 204 and 206 form a first compression zone and the sealing surfaces above the medial cells 208 and 210 form a second compression zone when the jaw members 292 and 294 are closed and clamped together on a vessel, the first compression zone being more flexible than the second compression zone. Again, if the jaw members 292 and 294 include the intermediate cells 212 and 214, the stiffness of the cells 212 and 214 can be selected to provide a desired transition from the first compression zone to the second compression zone.

The cells 204, 206, 208, 210, 212, 214 can be made from any suitable compliant materials such as elastomers. In some arrangements, none of the cells 204, 206, 208, 210, 212, 214 are electrically conductive. In other arrangements, some or all of the cells 204, 206, 208, 210, 212, 214 can be electrically conductive. Hence, when the jaw members 292 and 294 are connected to a generator that provides a source of electrical energy, a voltage with different potentials can be applied to the electrically conductive cells such that a current passes from one jaw member to the other jaw member through tissue clamped between the jaw members to coagulate or cut the tissue.

Figure 9:
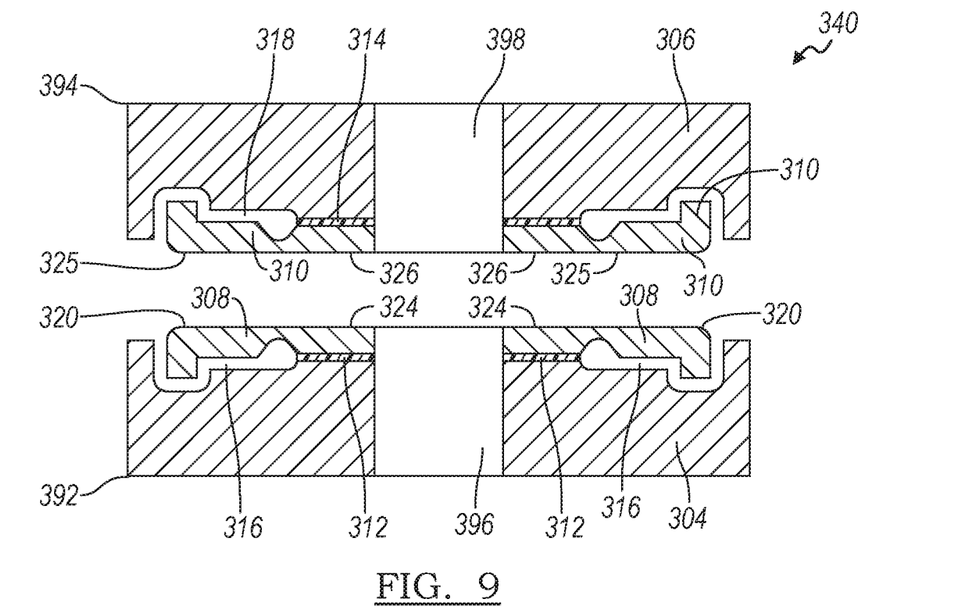
FIG. 9 illustrates a cross-sectional view of yet another set of jaws in accordance with the principles of the present invention.

Shown in FIG. 9 is another set of jaws 340 with a first jaw member 392 and a second jaw member 394 in accordance with the principles of the present invention. The first jaw member 392 includes a jaw body 304 and cantilever members 308 attached to the jaw body 304 on both sides of a slot 396 with a layer of material 312. The arrangement of the cantilever members 308 with respect to the jaw body 304 defines a cavity such as a gap 316 on each side of the slot 396 to enable the cantilever member 308 to flex with respect to the jaw body 304. As such, the first jaw member 392 includes lateral first sealing surfaces 320 and medial second sealing surfaces 324. Since the unattached region of the cantilever member 308 is able to flex into the gap 316, the first sealing surface 320 defines a more flexible region of the cantilever member 308 than the second sealing surface 324. Note that the stiffness of the layer of material 312 can be also be selected to adjust the stiffnesses of the first sealing surface 320 and the second sealing surface 324.

The second jaw member 394 includes a jaw body 306 and cantilever members 310 attached to the jaw body 306 on both sides of a slot 398 with a layer of material 314. The arrangement of the cantilever members 310 with respect to the jaw body 306 defines a cavity such as a gap 318 on each side of the slot 398 to enable the cantilever member 310 to flex with respect to the jaw body 306. As such, the second jaw member 394 includes lateral first sealing surfaces 325 and medial second sealing surfaces 326. Since the unattached region of the cantilever member 310 is able to flex into the gap 318, the first sealing surface 325 defines a more flexible region of the cantilever member 310 than the second sealing surface 326. Note that the stiffness of the layer of material 314 can be also be selected to adjust the stiffnesses of the first sealing surface 325 and the second sealing surface 326. The cantilevered members 308 and 310 can extend along a portion of or all of the jaw members 392 and 394.

Accordingly, the sealing surfaces 320 and 325 form a first compression zone and the sealing surfaces 324 and 326 form a second compression zone when the jaw members 392 and 394 are clamped together on a vessel, the first compression zone being more flexible than the second compression zone.

The jaw body 304 or cantilever members 308 or both the jaw body 304 and cantilever members 308 can be electrically conductive, and the jaw body 306 or cantilever members 310 or both the jaw body 306 and cantilever members 310 can be electrically conductive. Hence, when the jaw members 392 and 394 are connected to a generator that provides a source of electrical energy, a voltage with different potentials can be applied to the electrically conductive portions of the jaw members 392 and 394 such that a current passes from one jaw member to the other jaw member through tissue clamped between the jaw members to coagulate or cut the tissue.

Figure 10:
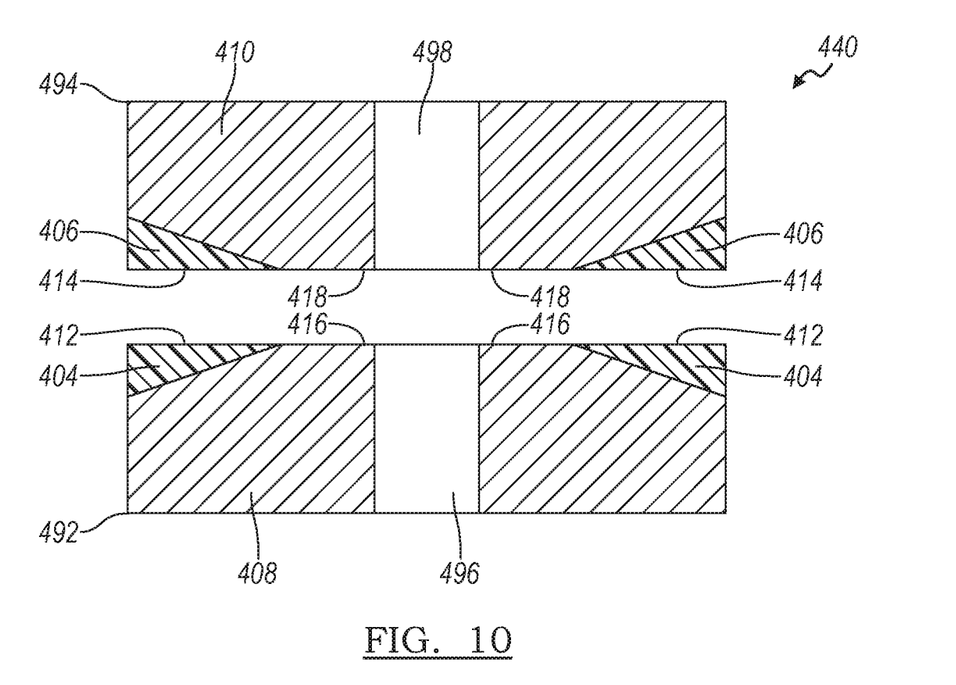
FIG. 10 illustrates a cross-sectional view of yet another set of jaws in accordance with the principles of the present invention.

Referring to FIG. 10, there is shown yet another set of jaws 440 in accordance with the principles of the present invention. The jaws 440 includes a first jaw member 492 and a second jaw member 494. The first jaw member 492 includes a jaw body 408 and wedges of pliable material 404, such as, for example, any compliant material including elastomers, attached to chamfered outer portions of the jaw body 408 on both sides of a slot 496. As such, the jaw member 492 includes a first sealing surface 412 on lateral portions or sections of the member 492, that is, on both sides of the slot 496, and a second sealing surface 412 on medial portions or sections on both sides of the slot 496. The second jaw member 492 includes a jaw body 410 and wedges of pliable material 406, such as, for example, any compliant material including elastomers, attached to chamfered outer portions of the jaw body 410 on both sides of a slot 498. Hence, the jaw member 494 includes a first sealing surface 414 on lateral portions or sections of the member 494, that is, on both sides of the slot 498, and a second sealing surface 418 on medial portions or sections on both sides of the slot 498. The wedges of pliable material 404 and 406 can extend along a portion of or all of the jaw members 492 and 494.

Accordingly, the first sealing surfaces 412 and 414 form a first compression zone above the pliable material 404 and 406, and the second sealing surfaces 416 and 418 form a second compression zone when the jaw members 492 and 494 are clamped together on a vessel. Because of the pliable or compliant nature of the material 404 and 406, the first compression zones produced by the compression surfaces 412 and 414 are more flexible than the second compression zones produced by the compression surfaces 416 and 418.

The jaw body 408 or pliable material 404 or both the jaw body 408 and pliable material 404 can be electrically conductive, and the jaw body 410 or pliable material 406 or both the jaw body 410 and pliable material 406 can be electrically conductive. Hence, when the jaw members 492 and 494 are connected to a generator that provides a source of electrical energy, a voltage with different potentials can be applied to the electrically conductive portions of the jaw members 492 and 494 such that a current passes from one jaw member to the other jaw member through tissue clamped between the jaw members to coagulate or cut the tissue.

Figure 11:
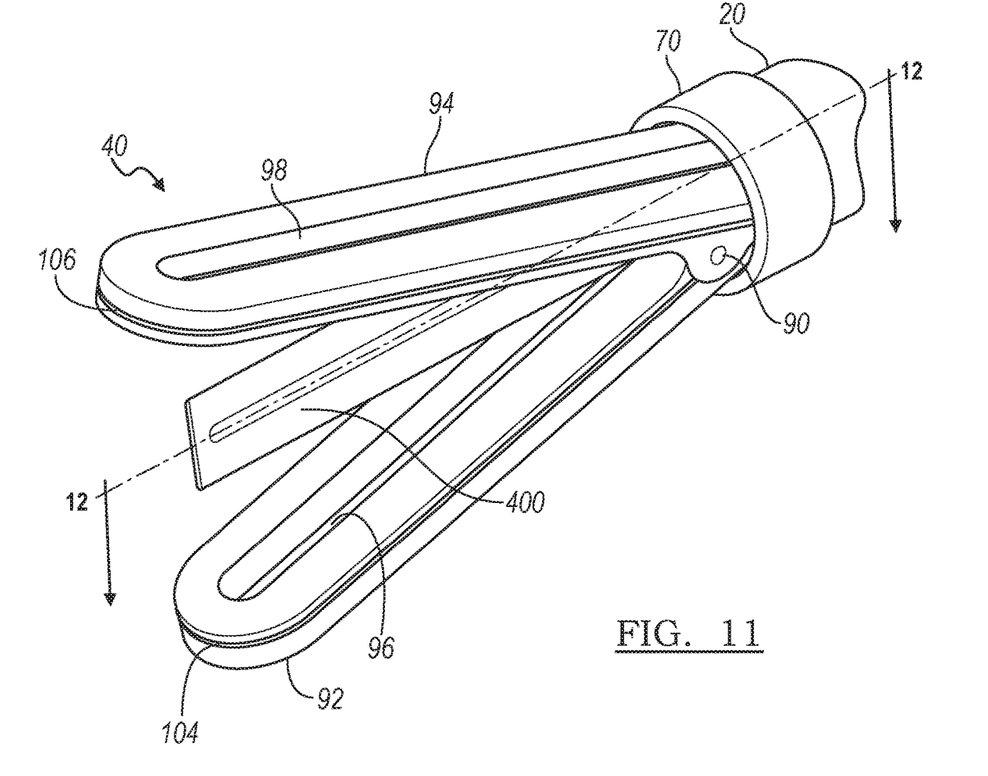
FIG. 11 illustrates a perspective view of the jaws shown in FIG. 6 with a cutting blade.
Figure 12:
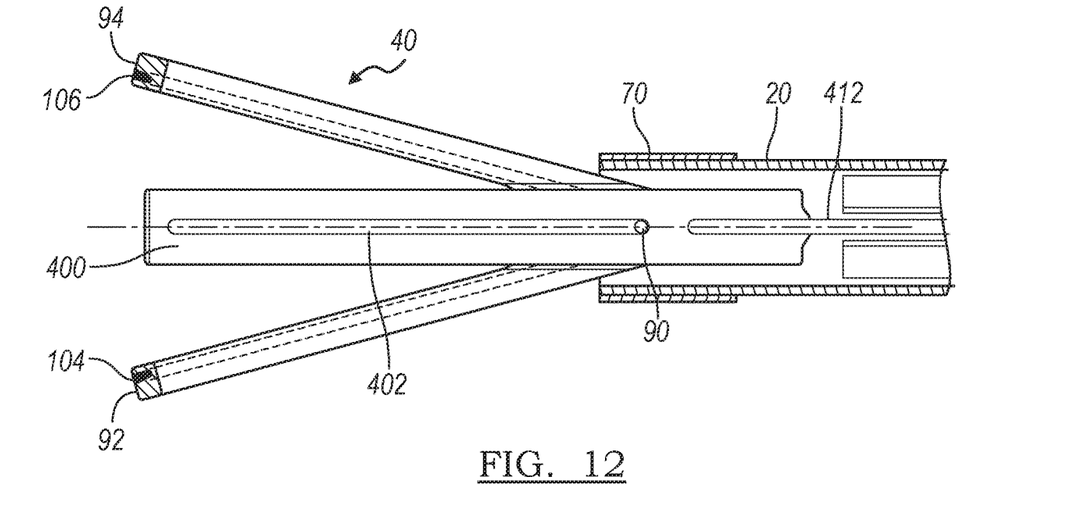
FIG. 12 illustrates a side view of the jaws shown in FIG. 6 with the cutting blade.

Any of the jaw arrangements 40, 240, 340 and 440 described previously can include a cutting blade. For example, as shown in FIGS. 11 and 12, the jaws 40 are shown with a blade 400. The blade 400 includes a slot 402 that engages with the pin 90 to allow the blade 400 to reciprocate along the pin 90. The blade 400 is connected to a blade shaft 412. Hence, axial movement of the blade shaft 412 results in reciprocating axial movement of the blade 400 along the slots 96 and 98 of the jaw members 92 and 94 to cut tissue clamped between the jaw members 92 and 94. A similar blade arrangement can be added to the jaws 240, 340 and 440.

Referring now to FIGS. 13, 14A, 14B, 15A and 15B, there is shown another set of jaws 540 in accordance with the principles of the present invention. The jaws 540 includes a first jaw member 592 and a second jaw member 594. The first jaw member 592 includes a lateral portion 502 and a medial or center portion 504 separated from the lateral portion 502 by a gap 508 to enable the lateral portion 502 to flex relative to the medial portion 504. The lateral portion 502 has a first sealing surface 506 and the medial portion 504 has a sealing surface 510. The second jaw member also has a lateral portion 521 with a first sealing surface 522 and a medial or center portion 526 with a second sealing surface 528. In various arrangements, the lateral portions 502 and 521 are made of a first material 516 and the medial portions 504 and 526 are made of a second material 518 that is stiffer than the first material 516.

The lateral portion 502 of the first jaw member includes a first set of non-conductive stops 512 and the medial portion 504 includes a second set of non-conductive stops 514. The first set of non-conductive stops 512 has a height of h1 and the second set of non-conductive stops 512 has a height of h2 that is less than the height h1. When the jaw members 592 and 594 are in an open position, the lateral portion 502 is coplanar with the center portion 504 and the lateral portion 521 is coplanar with the medial portion 526. As the jaw member 592 and 594 are closed together to clamp onto a vessel, the stops 512 deflect the lateral portions 502 and 521 prior to the first jaw member 592 and the second jaw member 594 fully closing such that the medial plates portions 504 and 526 contact each other if the medial portions 504 and 526 do not include the stops 514. If the medial portions 504 and 526 include the stops 514, the stops 512 of the lateral portion 502 make contact with the lateral portion 521 before the stops 514 of the medial portion 504 makes contact with the medial portion 526.

Figure 14A:
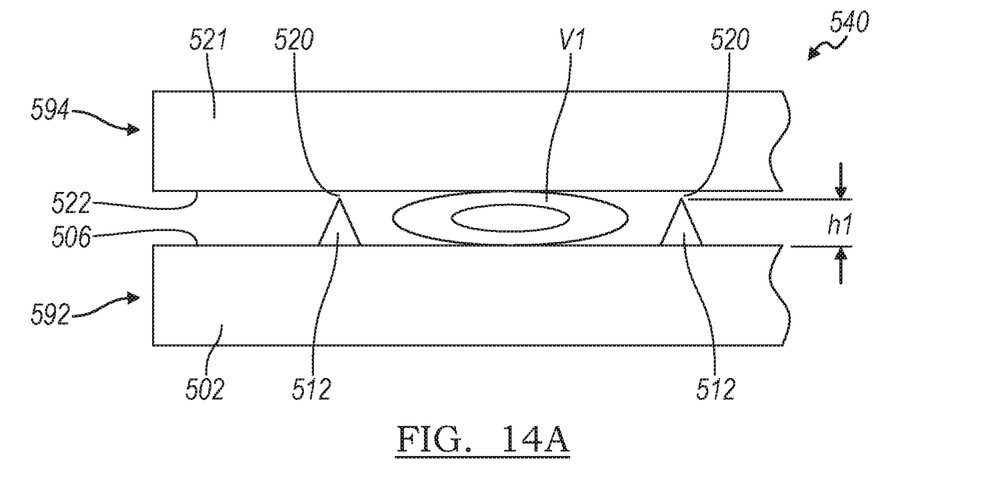
FIGS. 14A and 14B illustrate the jaws of FIG. 13 clamping onto a large vessel.
Figure 14B:
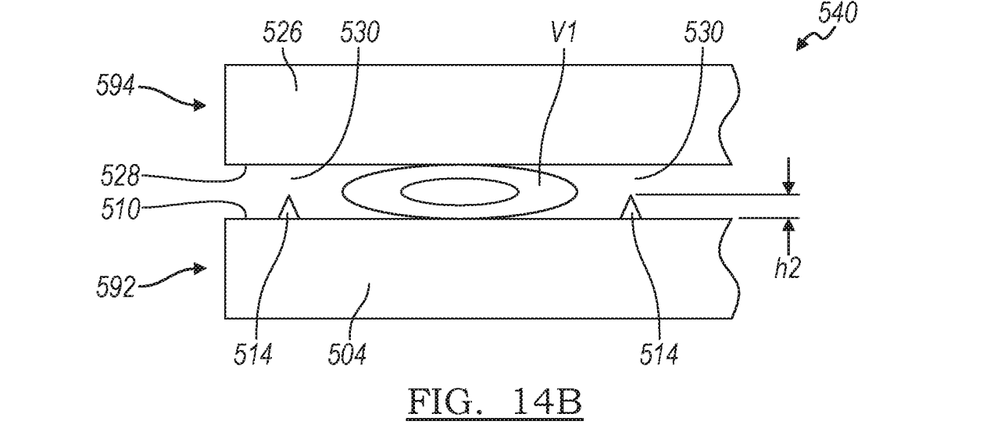

Hence, when the jaw members 592 and 594 clamp onto a large vessel, V1, as shown in FIGS. 14A and 14B, the gap 520 between the stops 512 and the lateral portion 521 is closed before the gap 530 between the stops 514 and the medial portion 526. The lateral portions 502 and 521, therefore, deflect relative to the medial portions 504 and 526 so that compressive forces are generated between the first sealing surfaces 506 and 522 and between the second sealing surfaces 510 and 528.

Figure 13:
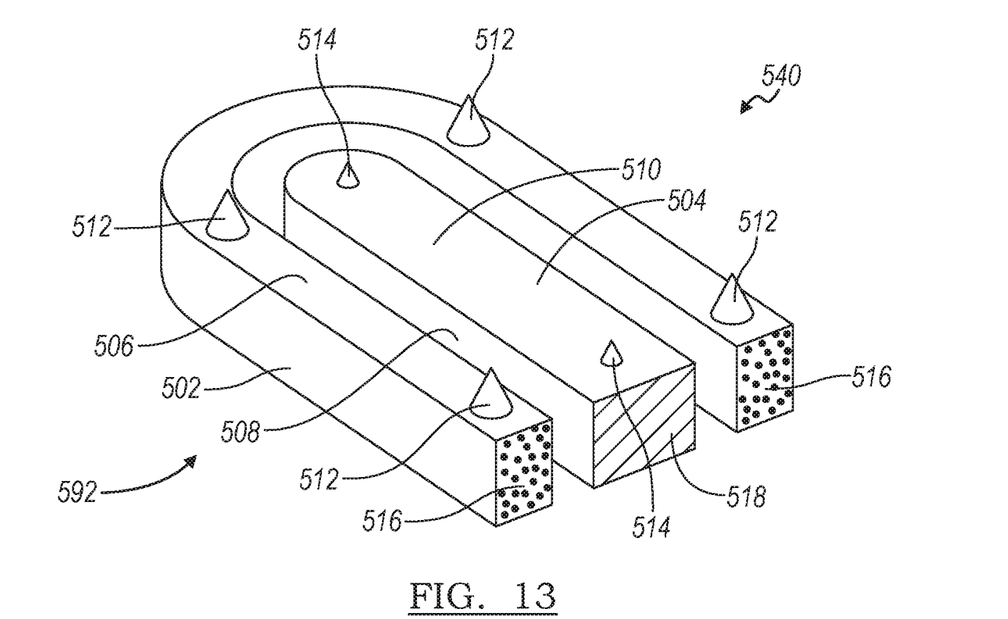
FIG. 13 illustrates a lower jaw of yet another set of jaws in accordance with the principles of the present invention.
Figure 15A:
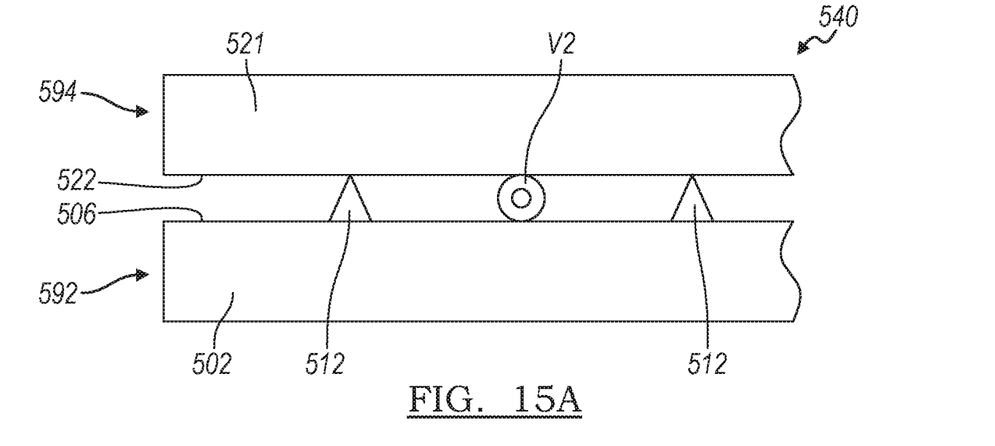
FIGS. 15A and 15B illustrate the jaws of FIG. 13 clamping onto a small vessel.
Figure 15B:
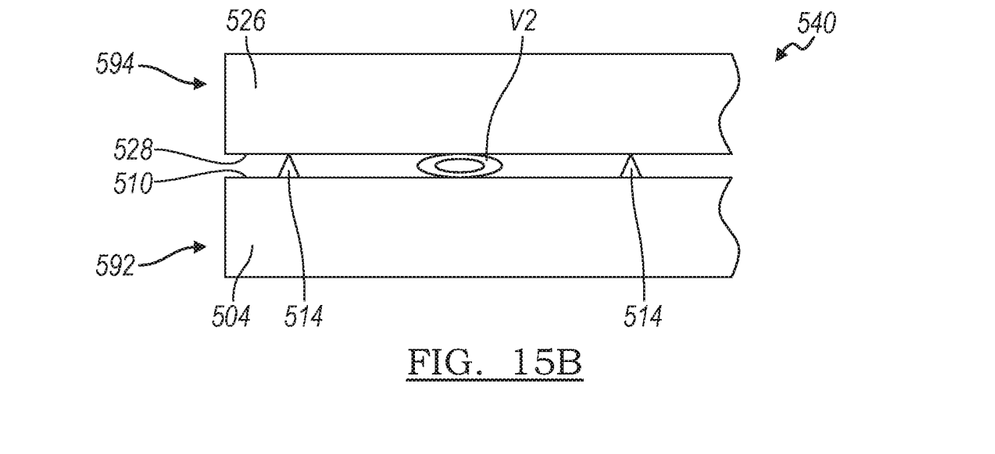

When the jaw members 592 and 594 clamp onto a smaller vessel, V2, as shown in FIGS. 15A and 15B, the stops 512 make contact with the lateral portion 521 to deflect the lateral portions 502 and 521 away from the medial portions 504 and 526 such that the stops 514 make contact with the medial portion 526 as well. Hence, when clamping onto a smaller vessel, V2, the compressive forces on the smaller vessel, V2, are generated primarily by the second sealing surfaces 510 and 528. Although four stops 512 are shown in FIG. 13, as few as one stop or more than four stops can be employed. Similarly, instead of the two stops 514 shown in FIG. 13, as few as one stop or more than two stops can be employed.

The lateral portion 502 or the medial portion 504 or both the lateral portion 502 and the medial portion 504 can be electrically conductive, and lateral portion 521 or the medial portion 526 or both the lateral portion 521 and the medial portion 526 can be electrically conductive. Hence, when the jaw members 592 and 594 are connected to a generator that provides a source of electrical energy, a voltage with different potentials can be applied to the electrically conductive portions of the jaw members 592 and 594 such that a current passes from one jaw member to the other jaw member through tissue clamped between the jaw members to coagulate or cut the tissue.

Figure 16:
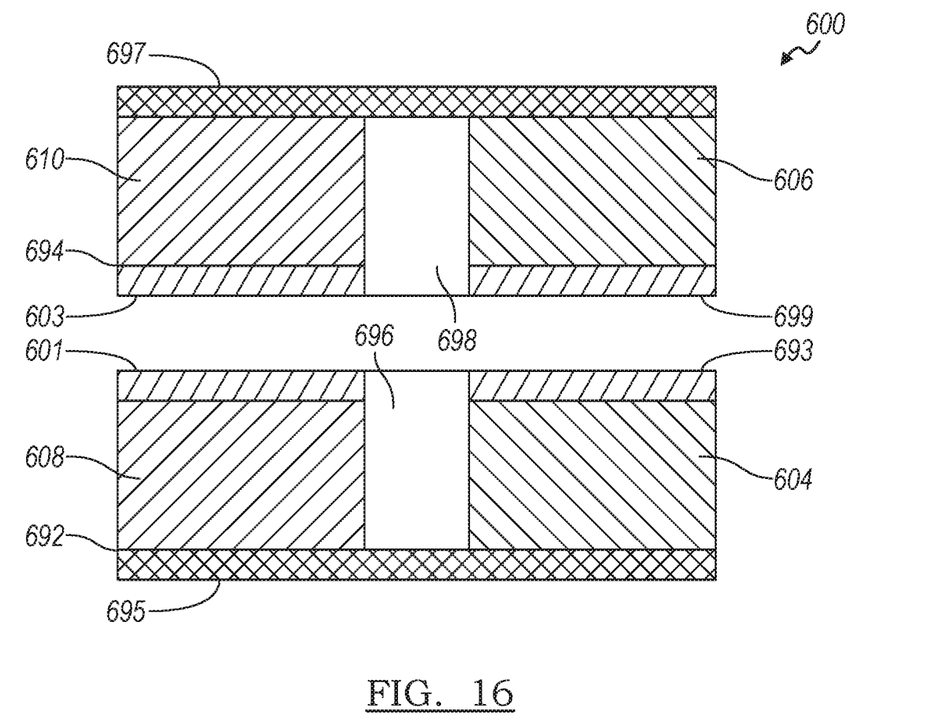
FIG. 16 illustrates a cross-sectional view of yet another set of jaws in accordance with the principles of the present invention.

Referring to FIG. 16, there is shown another set of jaws 600 in accordance with the principles of the present invention. The jaws 600 include a first jaw member 692 and a second jaw member 694. The first jaw member 692 includes a jaw body or support member 695 and a sealing plate 693 disposed on both sides of a slot 696. The exterior surface of the sealing plate 693 defines a sealing surface 601. A layer of pliable material 604 and 608 is disposed between the jaw body 695 and the sealing plate 693. The layer of pliable mater is made of separate cells with different stiffnesses, the cells 608 being stiffer than the cells 604.

The second jaw member 694 includes a jaw body 697 and a sealing plate 699 disposed on both sides of a slot 698. The exterior surface of the sealing plate 699 defines a sealing surface 603. A layer of pliable material 606 and 610 is disposed between the jaw body 697 and the sealing plate 699. The layer of pliable mater is made of separate cells with different stiffnesses, the cells 610 being stiffer than the cells 604. The layers of pliable material 604, 608 and 606, 610 can extend along a portion of or all of the jaw members 292 and 294.

Accordingly, the sealing surfaces above the cells 604 and 606 form a first compression zone and the sealing surfaces above the cells 608 and 610 form a second compression zone when the jaw members 692 and 694 are closed and clamped together on a vessel, the first compression zone being more flexible than the second compression zone.

The cells 604, 606, 608 and 610 can be made from any suitable compliant materials such as elastomers. In some arrangements, none of the cells 604, 606, 608 and 610 are electrically conductive. In other arrangements, some or all of the cells 604, 606, 608 and 610 can be electrically conductive. Hence, when the jaw members 692 and 694 are connected to a generator that provides a source of electrical energy, a voltage with different potentials can be applied to the electrically conductive cells such that a current passes from one jaw member to the other jaw member through tissue clamped between the jaw members to coagulate or cut the tissue.

The jaw arrangement 600 can include the cutting blade 400 shown previously in FIGS. 11 and 12. Again, the blade 400 includes the slot 402 that engages with the pin 90 to allow the blade 400 to reciprocate along the pin 90. The blade 400 is connected to the blade shaft 412. Hence, axial movement of the blade shaft 412 results in reciprocating axial movement of the blade 400 along the slots 696 and 698 of the jaw members 692 and 694 to cut tissue clamped between the jaw members 692 and 694.

Although the above-described jaws are directed to one jaw member pivotally attached to another jaw member, the present invention contemplates any type of jaw member that clamps onto tissue with another jaw member. For example, the jaw members can clamp onto tissue as the jaw members move toward each other in any suitable manner including translational and rotational movement. Further, as mentioned previously, various components of the any of the above-described jaw members can be electrically conductive. The components themselves can be electrically conductive electrodes or electrically conductive material can be added to the component to form an electrode on the component.

The description of the invention is merely exemplary in nature and variations that do not depart from the gist of the invention are intended to be within the scope of the invention. Such variations are not to be regarded as a departure from the spirit and scope of the invention.

What is claimed is:

1. A forceps end effector comprising:
   a shaft;
   first and second jaw members connected to the shaft, at least one of the first and second jaw members moveable between a first position wherein the first and second jaw members are spaced apart and a second position wherein the first jaw is moved towards the second jaw member and approaching a transverse plane defined between face portions of the first and second jaw members; and
   first and second tissue sealing surfaces each attached to a corresponding one of the first and second jaw members;
   wherein the first tissue sealing surface includes at least one compression feature configured to allow the first tissue sealing surface to compress more at an offset distance spaced apart from a medial plane than at the medial plane, the medial plane defined as:
      bisecting each of the shaft, the first jaw member, and the second jaw member; and
      being orthogonal to the transverse plane; and
   wherein the at least one compression feature includes a plurality of sections that are less rigid at the offset distance spaced apart from the medial plane than at the medial plane.

2. The forceps end effector of claim 1, wherein the plurality of sections include:
   a first section that is less rigid at a first offset distance spaced apart from the medial plane than at the medial plane; and
   a second section that is less rigid than the first section at a second offset distance spaced apart from the medial plane, the second offset distance being greater than the first offset distance.

3. The forceps end effector of claim 2, wherein the plurality of sections include:
   a third section that is less rigid than the second section at a third offset distance spaced apart from the medial plane, the third offset distance being greater than the second offset distance.

4. The forceps end effector of claim 1, wherein the at least one compression feature includes a cavity formed within a material of the first tissue sealing surface, wherein a compression force of tissue grasped between the first and second jaw members in the second position localizes more at the at least one compression feature at the offset distance spaced apart from the medial plane.

5. The forceps end effector of claim 4 wherein the cavity is filled with a flexible material including a polymer including at least one of polyurethane, nitrile, or polytetrafluoroethylene.

6. The forceps end effector of claim 4 wherein the cavity is filled with an elastic material.

7. The forceps end effector of claim 1 wherein the at least one compression feature includes a chamfer formed within a material of the first tissue sealing surface, the chamfer sized and shaped to mate with a corresponding wedge including flexible material.

8. The forceps end effector of claim 1 wherein at least one non-conductive stop is disposed on at least one of the first and second tissue sealing surfaces to prevent the two from contacting each other when the first and second jaw members are moved towards the second position.

9. The forceps end effector of claim 1, wherein at least one of the first and second tissue sealing surfaces include an electrode configured to receive a waveform from a source of electrosurgical energy to energize target tissue grasped between the first and second jaw members when the first and second jaw are moved towards the second position.

10. The forceps end effector of claim 1 wherein at least one of the first jaw member and the second jaw member includes a longitudinal slot and wherein the forceps end effector includes a blade configured to reciprocate within the slot.

11. The forceps end effector of claim 1, wherein the at least one compression feature includes at least one section that is increasingly less rigid at increasing offset distances spaced apart from the medial plane.

12. A forceps end effector comprising:
 a shaft;
 first and second jaw members connected to the shaft, at least one of the first and second jaw members moveable between a first position wherein the first and second jaw members are spaced apart and a second position wherein the first jaw is moved towards the second jaw member and approaching a transverse plane defined between face portions of the first and second jaw members; and
 first and second tissue sealing surfaces each attached to a corresponding one of the first and second jaw members;
 wherein the first tissue sealing surface includes at least one cavity formed within a material of the first tissue sealing surface, wherein a compression force of tissue grasped between the first and second jaw members in the second position localizes more at an offset distance spaced apart from a medial plane than at a location along the medial plane, the medial plane defined as:
  bisecting each of the shaft, the first jaw member, and the second jaw member; and
  being orthogonal to the transverse plane;
 wherein the at least one compression feature includes at least one section that is increasingly less rigid at increasing offset distances spaced apart from the medial plane.

13. The forceps end effector of claim 12 wherein the cavity is filled with a flexible material including a polymer including at least one of polyurethane, nitrile, or polytetrafluoroethylene.

14. The forceps end effector of claim 12 wherein the cavity is filled with an elastic material.

15. A forceps end effector comprising:
 a shaft;
 first and second jaw members connected to the shaft, at least one of the first and second jaw members moveable between a first position wherein the first and second jaw members are spaced apart and a second position wherein the first jaw is moved towards the second jaw member and approaching a transverse plane defined between face portions of the first and second jaw members; and
 first and second tissue sealing surfaces each attached to a corresponding one of the first and second jaw members, the first tissue sealing surface including at least one compression feature configured to allow the first tissue sealing surface to compress more at an offset distance spaced apart from a medial plane than at the medial plane, the at least one compression feature including at least one section that is increasingly less rigid at increasing offset distances spaced apart from the medial plane, the medial plane bisecting each of the shaft, the first jaw member, and the second jaw member, and the medial plane orthogonal to the transverse plane.

16. The forceps end effector of claim 15, wherein the at least one section includes:
 a first section that is less rigid at a first offset distance spaced apart from the medial plane than at the medial plane; and
 a second section that is less rigid than the first section at a second offset distance spaced apart from the medial plane, the second offset distance being greater than the first offset distance.

17. The forceps end effector of claim 16, wherein the at least one section includes:
 a third section that is less rigid than the second section at a third offset distance spaced apart from the medial plane, the third offset distance being greater than the second offset distance.

18. The forceps end effector of claim 15, wherein the at least one compression feature includes a cavity formed within a material of the first tissue sealing surface, wherein a compression force of tissue grasped between the first and second jaw members in the second position localizes more at the at least one compression feature located at an offset distance spaced apart from the medial plane.

19. The forceps end effector of claim 18 wherein the cavity is filled with a flexible material including a polymer including at least one of polyurethane, nitrile, or polytetrafluoroethylene.

20. The forceps end effector of claim 18, wherein the cavity is filled with an elastic material.

* * * * *